US011065611B2

(12) United States Patent
Wan

(10) Patent No.: US 11,065,611 B2
(45) Date of Patent: Jul. 20, 2021

(54) EMISSION CONTROL DURING CATALYST REGENERATION

(71) Applicant: Monsanto Technology LLC, St. Louis, MO (US)

(72) Inventor: Kam-To Wan, Town and Country, MO (US)

(73) Assignee: Monsanto Technology LLC, St. Louis, MO (US)

(*) Notice: Subject to any disclaimer, the term of this patent is extended or adjusted under 35 U.S.C. 154(b) by 0 days.

(21) Appl. No.: 16/339,430

(22) PCT Filed: Oct. 5, 2017

(86) PCT No.: PCT/US2017/055258
§ 371 (c)(1),
(2) Date: Apr. 4, 2019

(87) PCT Pub. No.: WO2018/067774
PCT Pub. Date: Apr. 12, 2018

(65) Prior Publication Data
US 2019/0283015 A1    Sep. 19, 2019

Related U.S. Application Data

(60) Provisional application No. 62/404,537, filed on Oct. 5, 2016.

(51) Int. Cl.
| | |
|---|---|
| *B01J 38/02* | (2006.01) |
| *B01J 38/12* | (2006.01) |
| *B01J 29/076* | (2006.01) |
| *C07C 37/00* | (2006.01) |
| *C07C 37/60* | (2006.01) |
| *C07C 17/358* | (2006.01) |
| *B01J 21/06* | (2006.01) |
| *B01J 23/22* | (2006.01) |
| *B01J 29/90* | (2006.01) |
| *B01J 38/06* | (2006.01) |
| *B01J 38/50* | (2006.01) |
| *F01N 9/00* | (2006.01) |
| *B01J 38/16* | (2006.01) |
| *B01J 38/14* | (2006.01) |
| *B01D 53/86* | (2006.01) |

(52) U.S. Cl.
CPC .......... *B01J 38/02* (2013.01); *B01D 53/8662* (2013.01); *B01J 21/063* (2013.01); *B01J 23/22* (2013.01); *B01J 29/076* (2013.01); *B01J 29/90* (2013.01); *B01J 38/06* (2013.01); *B01J 38/12* (2013.01); *B01J 38/14* (2013.01); *B01J 38/16* (2013.01); *B01J 38/50* (2013.01); *C07C 17/358* (2013.01); *C07C 37/00* (2013.01); *C07C 37/60* (2013.01); *F01N 9/00* (2013.01); *B01D 2255/2073* (2013.01); *B01D 2255/20723* (2013.01); *B01D 2255/20784* (2013.01); *B01D 2255/50* (2013.01); *B01D 2258/02* (2013.01); *Y02T 10/40* (2013.01)

(58) Field of Classification Search
None
See application file for complete search history.

(56) References Cited

U.S. PATENT DOCUMENTS

| | | | |
|---|---|---|---|
| 2,480,817 A | 8/1949 | Warren | |
| 2,651,659 A | 9/1953 | Warren | |
| 2,708,209 A | 5/1955 | Nicolaisen et al. | |
| 3,013,054 A | 12/1961 | Richter et al. | |
| 3,462,498 A | 8/1969 | Lowe et al. | |
| 3,464,930 A | 9/1969 | Friedrichsen et al. | |
| 4,059,675 A | 11/1977 | Yang et al. | |
| 4,568,777 A | 2/1986 | Baltes et al. | |
| 4,801,567 A | 1/1989 | Moorehead | |
| 4,935,561 A * | 6/1990 | Eichler | C07C 17/358 570/202 |
| 5,118,876 A | 6/1992 | Zinnen et al. | |
| 5,176,897 A | 1/1993 | Lester | |
| 5,283,041 A * | 2/1994 | Nguyen | B01D 53/8662 423/240 S |
| 5,292,704 A | 3/1994 | Lester | |
| 5,648,562 A | 7/1997 | Henrick | |
| 5,837,636 A | 11/1998 | Sechrist et al. | |
| 6,323,377 B1 | 11/2001 | Scheuerman et al. | |
| 2010/0130774 A1 | 5/2010 | Wan et al. | |
| 2015/0352492 A1 | 12/2015 | Anderson et al. | |

FOREIGN PATENT DOCUMENTS

| | | |
|---|---|---|
| CN | 104741117 A | 7/2015 |
| CN | 105921161 A | 9/2016 |
| WO | 2016/054506 A1 | 4/2017 |

OTHER PUBLICATIONS

Banares, M.A., et al., "The Role of Vanadium Oxide on the Titania Transformation under Thermal Treatments and Surface Vanadium States," 1996, J Solid State Chem, 124:69-76, Article No. 0209, 8 pages.

Cho, C.H., et al., "Development of New Vanadium-Based Oxide Catalysts for Decomposition of Chlorinated Aromatic Pollutants," 2002, Environ Sci Technol, 36/7:1600-1606, Abstract Only.

Debecker, D.P., et al., "Evaluation of PCDD/F oxidation catalysts: confronting studies on model molecules with tests on PCDD/F-containing gas stream," 2011, Chemosphere, 82/9:1337-1342, 6 pages.

(Continued)

*Primary Examiner* — Medhanit W Bahta
(74) *Attorney, Agent, or Firm* — Stinson LLP

(57) ABSTRACT

Catalyst regeneration processes that include measures for controlling emissions generated during the regeneration are described. The present invention further relates to catalytic processes for producing various chlorinated aromatic compounds that include provisions for controlling emissions during catalyst regeneration.

20 Claims, No Drawings

(56) References Cited

OTHER PUBLICATIONS

Habersberger, K., et al., "Synthesis of ZSM zeolites modified with vanadium and their application in the catalytic oxidation of butadiene," 1989, Reaction Kinetics and Catalysis Letters, 39/1:95-100, Abstract only.

Krishnamoorthy, S., et al., "Catalytic oxidation of 1,2-dichlorobenzene over V2O5/TiO2-based catalysts," 1998, Catalysis Today, 40/1:39-46, Abstract only.

Liljelind, P., et al., "Synthesis of ZSM zeolites modified with vanadium and their application in the catalytic oxidation of butadiene," 2001, Chemosphere, 42:615-623, 9 pages.

Maaskant, O.L., et al., "A Catalytic System for Nox and Dioxins Removal, Applications, Performance and Costs," Mar. 21-22, 2011, Conference on NOx/NO2 Control Techniques, CRI Catalyst UK, Ademe Conference—Rev. 1, Paris, France, 21 pages.

Petras, M. et al., "High-temperature Interaction of Vanadium Pentoxide with H-ZSM-5 Zeolite. ESR and IR Study," 1992, J Phys Chem, 96/4:1805-1809, p. 1 Only.

Tang, H.S., "The Shell Dioxin Destruction System," Feb. 26-27, 2003, Solid & Hazardous Waste Management Conference, Singapore, 10 pages.

Wark, M., et al., "Investigation of zeolites by photoelectron and ion scattering spectroscopy Part IV XPS studies of vanadium-modified zeolites," 1998, J Chem Soc, Faraday Trans, 94:2033-2041, 9 pages.

Zhang, S.G., et al., "Characterization of Vanadium Oxide/ZSM-5 Zeolite Catalysts Prepared by the Solid-State Reaction and Their Photocatalytic Reactivity: In Situ Photoluminescence, XAFS, ESR, FT-IR, and UV-vis Investigations," 1998, J Phys Chem B, 102/29:5590-5594, Abstract only.

International Search Report and Written Opinion issued in PCT/US2017/55258, dated Jan. 2, 2018, 9 pages.

* cited by examiner

EMISSION CONTROL DURING CATALYST REGENERATION

REFERENCE TO RELATED APPLICATIONS

The present application is the 371 National Stage Application of International Patent Application Serial No. PCT/US2017/055258, filed Oct. 5, 2017, which claims the benefit of U.S. Provisional Application Ser. No. 62/404,537, filed Oct. 5, 2016, the entire contents of which are incorporated herein by reference.

FIELD OF THE INVENTION

The present invention relates to catalyst regeneration processes that include measures for controlling emissions generated during the regeneration. The present invention also relates to catalytic processes for producing various chlorinated aromatic compounds that include provisions for controlling emissions during catalyst regeneration.

BACKGROUND OF THE INVENTION

Chlorinated mono-aromatic compounds are useful intermediates in the preparation of a variety of chemical products. For example, dichlorophenols are used in the productions of certain herbicides. For example, 2,4-dichlorophenoxyacetic acid (2,4-D) can be prepared from 2,4-dichlorophenol. See U.S. Pat. Nos. 2,480,817 and 2,651,659. Also, 3,6-dichloro-2-methoxybenzoic acid (dicamba) can be prepared from 2,5-dichlorophenol. See, for example, U.S. Pat. Nos. 3,013,054 and 5,648,562.

Some processes for producing chlorinated mono-aromatic compounds involve heterogeneous catalysis. For example, U.S. Pat. No. 4,568,777 describes a process for the isomerization of mono- or dichlorophenols, including 2,4-dichlorophenol, using certain types of zeolite catalysts. As time-on-stream increases, the catalyst may deactivate to a certain extent (e.g., by the accumulation of carbonaceous deposits or coking) which reduces catalyst performance. Eventually, the catalyst may need to be replaced or regenerated when acceptable catalyst performance cannot be maintained. To enhance process economics, regeneration of the catalysts is often preferred over catalyst replacement.

Generally, regenerating catalysts involves removing carbonaceous deposits and/or other components adsorbed on the catalysts. For instance, some processes for regenerating the catalysts include heating the catalysts to relatively high temperatures in the presence of oxygen to remove carbon deposits and/or desorb bound compounds. Although catalyst regeneration is typically beneficial to process economics, some of these processes result in emissions that must be controlled or managed because they may be unsuitable for release to the environment. In the case of catalysts used in producing chlorinated mono-aromatic compounds, regeneration can lead to emissions of the chlorinated aromatic compounds. Thus, there remains a need for regeneration processes of these catalysts that include cost-effective emission controls for chlorinated aromatic compounds.

SUMMARY OF THE INVENTION

Briefly, in some aspects, the present invention relates to processes for regenerating heterogeneous process catalysts comprising a chlorinated aromatic compound adsorbed thereon, wherein the process includes provisions for controlling emissions generated during regeneration. The processes comprise heating the heterogeneous process catalyst at an elevated temperature (e.g., from about 400° C. to about 1000° C.) in the presence of oxygen to remove at least a portion of the chlorinated aromatic compound from the heterogeneous process catalyst and produce a regenerated heterogeneous process catalyst and a regeneration effluent; and contacting the regeneration effluent with an oxidation catalyst comprising at least one metal oxide (e.g., vanadium oxide) to form an oxidation effluent comprising carbon dioxide, water, and hydrochloric acid.

In other aspects, the present invention relates to processes for producing chlorinated phenols such as 2,5-dichlorophenol that also include provisions for controlling emissions during catalyst regeneration. One process comprises contacting a feed comprising 2,4-dichlorophenol with an isomerization catalyst comprising a zeolite in a reactor system to form a reaction product comprising 2,5-dichlorophenol, wherein the reactor system further comprises an oxidation catalyst comprising at least one metal oxide. Another process comprises contacting a feed comprising 1,4-dichlorobenzene with an oxidizing agent in the presence of a hydroxylation catalyst comprising a zeolite in a reactor system to form a reaction product comprising 2,5-dichlorophenol, wherein the reactor system further comprises an oxidation catalyst comprising at least one metal oxide.

Other objects and features will be in part apparent and in part pointed out hereinafter.

DESCRIPTION OF THE PREFERRED EMBODIMENTS

Generally, the present invention relates to catalyst regeneration processes that include one or more measures for controlling emissions generated during the regeneration. The present invention also relates to catalytic processes for producing various chlorinated mono-aromatic compounds that include provisions for controlling emissions during catalyst regeneration. These processes are convenient and highly effective in controlling emissions during catalyst regeneration while enhancing process economics and reducing wastes.

Catalyst Regeneration Process

Various processes in accordance with the present invention are generally directed to regeneration of solid heterogeneous process catalysts, particularly catalysts that comprise one or more chlorinated aromatic compounds adsorbed thereon during normal process operations. One process for regeneration of a heterogeneous process catalyst comprising a chlorinated aromatic compound adsorbed thereon comprises heating the heterogeneous process catalyst at an elevated temperature in the presence of oxygen to regenerate the catalyst and form a regeneration effluent; and contacting the regeneration effluent with an oxidation catalyst to form an oxidation effluent.

During the regeneration process, the heterogeneous process catalyst is heated to a temperature sufficient to substantially remove the compounds adsorbed thereon, and produce a regenerated heterogeneous process catalyst and a regeneration effluent. The regeneration effluent may contain one or more chlorinated aromatic compounds removed from the heterogeneous process catalyst. The temperature required for regeneration can be dependent on the type of process catalyst, but is typically within the temperature range of from about 400° C. to about 1000° C., from about 500° C. to about 900° C., from about 500° C. to about 800° C., or from about 500° C. to about 700° C.

Generally, the oxidation catalyst is effective in converting one or more of the components of the regeneration effluent to products of oxidation including carbon dioxide, water, and hydrochloric acid. It should be understood that the regeneration effluent contacted with the oxidation catalyst does not necessarily have to be isolated as a discrete stream or emission. Typically, the oxidation catalyst comprises at least one metal oxide. In various embodiments, the oxidation catalyst comprises at least one metal oxide selected from the group consisting of vanadium oxide, chromium oxide, manganese oxide, and mixtures thereof. In certain embodiments, the oxidation catalyst comprises vanadium oxide. The metal oxides referred to herein can include one or more oxides of different oxidation states.

The oxidation catalyst is a heterogeneous catalyst and in various embodiments, the oxidation catalyst comprises at least one metal oxide (e.g., vanadium oxide) on a support. A wide range of supports can be used. For example, the oxidation catalyst can comprise at least one material selected from the group consisting of alumina, titania, silica, zirconia, carbon, zeolite, and combinations thereof. In some embodiments, the support of the oxidation catalyst comprises titania. In other embodiments, the support of the oxidation catalyst comprises alumina. One preferred oxidation catalyst comprises vanadium oxide on a support comprising titania. Specific examples of metal oxide-containing heterogeneous catalysts include CK-305 (chromium oxide on alumina), CK-306 (chromium oxide/palladium on alumina), and CK-395 (manganese oxide on alumina) available from Haldor Topsoe and metal oxide catalysts (e.g., vanadium oxide on titania) available from CRI Catalyst.

The oxidation catalyst can be situated with respect to the heterogeneous process catalyst in a variety of different ways. In various embodiments, the oxidation catalyst is mixed with the heterogeneous process catalyst (i.e., a physical mixture of distinct catalyst compositions). The oxidation catalyst can also be incorporated onto or supported on the heterogeneous process catalyst (i.e., as a co-catalyst). The oxidation catalyst and heterogeneous process catalyst can be positioned in a stacked or staged reactor system configuration. Accordingly, in some embodiments, a first stage comprises the heterogeneous process catalyst and a second stage comprises the oxidation catalyst, wherein the second stage is downstream of the first stage with respect to the direction of flow through the reactor system.

The heterogeneous process catalyst can be any catalyst that is suitable for oxidative regeneration at elevated temperature and comprises one or more chlorinated aromatic compounds adsorbed thereon. As noted, some processes for producing chlorinated mono-aromatic compounds use catalysts comprising a zeolite. Accordingly, in various embodiments, the heterogeneous process catalyst comprises a zeolite as described in greater detail below.

The catalyst regeneration processes of the present invention, which include measures for controlling emissions generated during regeneration, are suitable for controlling emissions of various types of chlorinated aromatic compounds that can be adsorbed on the heterogeneous process catalyst during normal process operations. For example, in various embodiments, the chlorinated aromatic compound comprises at least one compound selected from the group consisting of 2,3,4-trichlorophenol; 2,3,5-trichlorophenol; 2,3,6-trichlorophenol; 2,4,5-trichlorophenol; 2,4,6-trichlorophenol; 3,4,5-trichlorophenol; 2,3-dichlorophenol; 2,4-dichlorophenol; 2,5-dichlorophenol; 2,6-dichlorophenol; 3,4-dichlorophenol; 3,5-dichlorophenol; 2-chlorophenol; 3-chlorophenol; 4-chlorophenol; 1,2,3-trichlorobenzene; 1,2,4-trichlorobenzene; 1,3,5-trichlorobenzene; 1,2-dichlorobenzene; 1,3-dichlorobenzene; 1,4-dichlorobenzene; and oxidation and chlorination products thereof; and mixtures thereof. In addition to controlling emissions of compounds initially adsorbed on the heterogeneous process catalyst, the processes of the present invention are also effective in controlling emissions of products produced from these compounds during oxidative regeneration.

Processes of the present invention can further comprise one or more pre-cleaning steps that desorb at least a portion of the chlorinated aromatic compound from the heterogeneous process catalyst prior to catalyst regeneration (e.g., heating at a temperature of from about 400° C. to about 1000° C.). Accordingly, in various embodiments, the process further comprises desorbing at least a portion of the chlorinated aromatic compound from the heterogeneous process catalyst at a temperature no greater than about 350° C. prior to the step of heating the heterogeneous process catalyst at the temperature of from about 400° C. to about 1000° C. The pre-cleaning can be achieved by utilizing one or more techniques.

For example, desorbing at least a portion of the chlorinated aromatic compound from the heterogeneous process catalyst can comprise one or more of the following techniques:
(a) applying vacuum to the heterogeneous process catalyst;
(b) contacting the heterogeneous process catalyst with steam; and/or
(c) contacting the heterogeneous process catalyst with a non-chlorinated organic compound.

Typically, the pre-cleaning step is conducted in an inert or non-oxidative atmosphere, such as a nitrogen-containing atmosphere.

In embodiments where desorbing at least a portion of the chlorinated aromatic compound from the heterogeneous process catalyst comprises contacting the heterogeneous process catalyst with steam, the temperature of the steam is typically no greater than about 300° C.

In embodiments where desorbing at least a portion of the chlorinated aromatic compound from the heterogeneous process catalyst comprises contacting the heterogeneous process catalyst with a non-chlorinated organic compound, the non-chlorinated organic compound can be selected from the group consisting of aromatics, amines, and mixtures thereof. The non-chlorinated organic compound is selected such that the compound is preferentially adsorbed onto the heterogeneous process catalyst relative to the chlorinated aromatic compound. Upon contact with the heterogeneous process catalyst, the non-chlorinated organic compound displaces chlorinated aromatic compound from the catalyst.

The chlorinated aromatic compounds desorbed during pre-cleaning can be collected and recycled for further use or processing.

Isomerization Processes

Catalytic isomerization processes for producing monochlorophenols (e.g., 3-chlorophenol) and dichlorophenols (e.g., 2,5-dichlorophenol) are described in U.S. Pat. No. 4,568,777 and International Patent Application Publication WO 2016/054506, which are incorporated herein by reference. In general, these processes employ certain zeolite catalysts which, following prolonged use on-stream can be regenerated.

Some of these processes involve the production of 2,5-dichlorophenol by the isomerization of 2,4-dichlorophenol according to the reaction scheme shown below:

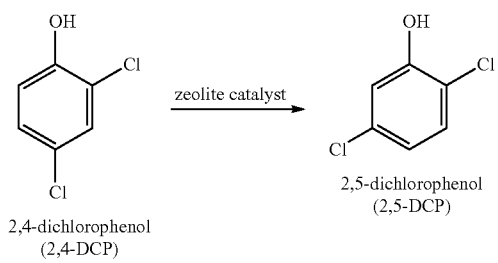 [SMILES: Oc1ccc(Cl)cc1Cl ; Oc1cc(Cl)ccc1Cl]

2,4-dichlorophenol
(2,4-DCP)

2,5-dichlorophenol
(2,5-DCP)

Accordingly, various processes of the present invention for producing 2,5-dichlorophenol which include provisions for controlling emissions during catalyst regeneration comprise contacting a feed comprising 2,4-dichlorophenol with an isomerization catalyst comprising a zeolite in a reactor system comprising an isomerization zone to form a reaction product comprising 2,5-dichlorophenol, wherein the reactor system further comprises an oxidation catalyst comprising at least one metal oxide as previously described herein (e.g., comprising vanadium oxide on a titania support). In general, the process described herein can be conducted in known industrial reactor system formats including fixed beds.

Suitable zeolites include medium and large pore size zeolites. Suitable medium pore size zeolites include pentasil zeolites such as ZSM-5 and ZSM-11 and large pore size zeolites include Beta zeolites and faujasite zeolites, such as zeolite Y. Thus, the zeolite catalyst can comprise at least one alumino-silicate zeolite selected from the group consisting of ZSM, Beta, Y zeolites, and mixtures thereof. In various embodiments, the isomerization catalyst comprises a promoted or modified zeolite such as a boron-promoted zeolite or a metal-promoted zeolite selected from the group consisting of titanium-silicates, alumino-silicates, iron-silicates, and gallium-silicate.

The isomerization catalyst can comprise a zeolite in acid form. For example, the zeolite can includes the acid form of a medium pore size zeolite such as ZSM-5 zeolite (e.g., HZSM-5) or a large pore size zeolite including Beta zeolites and faujasite zeolite such as zeolite Y. An acid form (also known as proton form or hydrogen form) of a zeolite can be prepared by calcining an ammonium form of zeolite catalyst at elevated temperature (e.g., in the range of from about 500° C. to about 1000° C. Also, an acid form of a zeolite catalyst can also be prepared from a sodium form of zeolite. In this technique, the sodium form is subject to ion exchange with an ammonium salt to form the ammonium form of the zeolite. Subsequently, the ammonium form can be calcined to the acid form.

The isomerization processes can be conducted over a broad temperature range. Generally, the catalyst is contacted with a feed comprising 2,4-dichlorophenol at a catalyst temperature in the range of from about 220° C. to about 550° C., from about 220° C. to about 450° C., from about 220° C. to about 350° C., from about 220° C. to about 300° C., from about 220° C. to about 290° C., from about 220° C. to about 285° C., from about 250° C. to about 550° C., from about 250° C. to about 450° C., from about 250° C. to about 350° C., from about 250° C. to about 300° C., from about 250° C. to about 290° C., from about 250° C. to about 285° C., from about 270° C. to about 450° C., from about 270° C. to about 350° C., from about 270° C. to about 300° C., from about 270° C. to about 290° C., from about 270° C. to about 285° C., from about 275° C. to about 550° C., from about 275° C. to about 285° C., from about 200° C. to about 450° C., from about 250° C. to about 375° C., from about 270° C. to about 350° C., from about 280° C. to about 325° C., or from about 290° C. to about 310° C.

The feed comprising 2,4-dichlorophenol can be introduced to the isomerization zone as a gas or a liquid. When gaseous 2,4-dichlorophenol is introduced into the isomerization reaction zone containing the zeolite catalyst, the partial pressure of 2,4-dichlorophenol in the feed gas can be at least about 0.05 kPa, at least about 0.5 kPa, at least about 1 kPa. The partial pressure of 2,4-dichlorophenol in the feed gas to the isomerization reaction zone is typically from about 0.05 kPa to about 10 kPa, from about 0.5 kPa to about 10 kPa, or from about 1 kPa to about 10 kPa. Also, the isomerization reaction can be conducted in the presence of an inert gas such as nitrogen or argon gas.

The oxidation catalyst that is present in the reactor system can be situated in a variety of different ways. For example, the oxidation catalyst can be situated such that it is in contact with the feed and/or reaction product of the isomerization, generally so long as the oxidation catalyst does not cause any significant negative effects to the efficacy of the isomerization reaction (e.g., within the isomerization zone). Thus, one approach to this arrangement is mixing the oxidation catalyst with the isomerization catalyst (e.g., in a fixed bed comprising the catalysts in the isomerization zone). Another arrangement includes a stacked or staged reactor system configuration. In these embodiments, a first stage comprises the isomerization catalyst and a second stage comprises the oxidation catalyst, wherein the second stage is downstream of the first stage with respect to the direction of flow through the reactor system. Other approaches include incorporating or supporting the oxidation catalyst on the isomerization catalyst (i.e., as a co-catalyst). In these embodiments where the oxidation catalyst is in contact with the feed and/or isomerization reaction product, the temperature of the oxidation catalyst is typically maintained at a temperature of no less than about 220° C. (e.g., to prevent condensation of feed/product constituents on the catalysts).

The oxidation catalyst can be also positioned such that it is not in contact with the feed and/or reaction product of the isomerization. For example, in the staged reactor system configuration, the first stage and second stage can be configured such that the reaction product comprising 2,5-dichlorophenol can optionally bypass the second stage. A further approach involves transferring the isomerization catalyst from the isomerization zone to a catalyst regeneration zone wherein the catalyst regeneration zone comprises the oxidation catalyst.

The isomerization process for producing 2,5-dichlorophenol typically further comprises the step of regenerating the isomerization catalyst during the course of isomerization process operations as discussed herein, wherein the isomerization catalyst to be regenerated comprises a chlorinated aromatic compound adsorbed thereon. The regeneration proceeds as discussed herein. For example, in various embodiments, regenerating the isomerization catalyst comprises heating the isomerization catalyst at an elevated temperature (e.g., of from about 400° C. to about 1000° C.) in the presence of oxygen to remove at least a portion of the chlorinated aromatic compound from the isomerization catalyst and produce a regenerated isomerization catalyst and a regeneration effluent; and contacting the regeneration effluent with the oxidation catalyst comprising the at least one metal oxide to form an oxidation effluent comprising carbon dioxide, water, and hydrochloric acid. The regeneration process can also further comprise a pre-cleaning step as described above to desorb at least a portion of the chlorinated aromatic compound from the isomerization catalyst prior to the step of heating the isomerization catalyst at the elevated temperature in the presence of oxygen. Any one of more of the pre-cleaning techniques discussed herein can be utilized. The chlorinated aromatic compounds desorbed during pre-cleaning can be collected and recycled back to the isomerization zone.

The isomerization catalyst to be regenerated comprises one or more chlorinated aromatic compounds adsorbed thereon. In various embodiments of the process for producing 2,5-dichlorophoneol, the chlorinated aromatic compound adsorbed thereon comprises at least one phenol compound selected from the group consisting of 2,3-dichlorophenol; 2,4-dichlorophenol; 2,5-dichlorophenol; 2,6-dichlorophenol; 3,4-dichlorophenol; 2-chlorophenol; 3-chlorophenol; 4-chlorophenol; and oxidation and chlorination products thereof; and mixtures thereof. In addition to controlling emissions of compounds initially adsorbed on the isomerization catalyst, the processes of the present invention are also effective in controlling emissions of products produced from these compounds during oxidative regeneration.

Another isomerization process of the present invention includes a process for producing 3-chlorophenol with provisions for controlling emissions during catalyst regeneration. In these embodiments, the process comprises contacting a feed comprising 2-chlorophenol and/or 4-chlorophenol with an isomerization catalyst comprising a zeolite in a reactor system comprising an isomerization zone to form a reaction product comprising 3-chlorophenol, wherein the reactor system further comprises an oxidation catalyst comprising at least one metal oxide as described herein. Features of the catalysts, process conditions, regeneration steps, and other details discussed above likewise apply to this process.

Hydroxylation Processes

Additional processes in accordance with the present invention are directed to preparing 2,5-dichlorophenol from 1,4-dichlorobenzene which include provisions for controlling emissions during oxidative catalyst regeneration. In general, these processes include hydroxylating 1,4-dichlorobenzene with an oxidizing agent in the presence of a zeolite catalyst to form 2,5-dichlorophenol. For example, see WO 2016/054506. The reaction proceeds according to the scheme shown below.

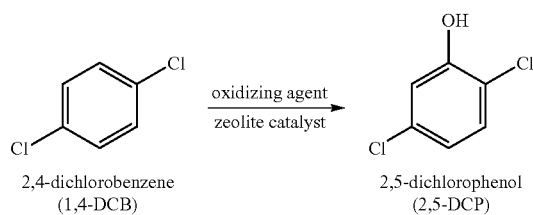 [SMILES: Clc1ccc(Cl)cc1 ; Oc1cc(Cl)ccc1Cl]

2,4-dichlorobenzene (1,4-DCB)    2,5-dichlorophenol (2,5-DCP)

Accordingly, various processes of the present invention for producing 2,5-dichlorophenol which include provisions for controlling emissions during regeneration comprise contacting a feed comprising 1,4-dichlorobenzene with an oxidizing agent in the presence of a hydroxylation catalyst comprising a zeolite in a reactor system comprising a hydroxylation zone to form a reaction product comprising 2,5-dichlorophenol, wherein the reactor system further comprises an oxidation catalyst comprising at least one metal oxide as previously described herein (e.g., comprising vanadium oxide on a titania support).

The hydroxylation catalyst can be a metal-promoted zeolite or a zeolite in acid form. Metal-promoted zeolites include, for example, titanium silicates such as TS-1 and TS-PQ, vanadium-containing zeolites such as V-Beta, and metal-promoted alumino-silicates such as Fe-ZSM-5 and Fe-ZSM-11. Suitable zeolites, which can be metal-promoted or in acid form, include pentasil and faujasite zeolites such as zeolite Beta, ZSM type zeolites, zeolite Y, and mixtures thereof. Acid form ZSM type zeolites include, for example, HZSM-5 and HZSM-11. In various hydroxylation processes of the present invention, the zeolite includes a metal-promoted alumino-silicate, particularly Fe-ZSM-5.

It has been found that the activation temperature and method can impact the performance of the zeolite catalyst. In some instances, higher calcination temperatures of the fresh zeolite catalyst prior to use or after regeneration beneficially reduces the isomerization and decomposition of the 2,5-dichlorophenol product to off-target reaction products such as 2,4-dichlorophenol and monochlorophenols. In some instances, the catalyst activated either at a higher temperature or at slightly lower temperature by steam may beneficially increase the stability of the catalyst during the hydroxylation reaction. Without being bound by theory, it is believed that the steam activation of the catalyst may create meso-porosity in the zeolite structure, which prevents the catalyst from deactivating by coking. Accordingly, the zeolite can be first calcined, then activated and calcined again prior to use.

For example, in one catalyst preparation method, the zeolite (e.g. $NH_4$-ZSM-5) can be first calcined in air to convert to the zeolite to the acid form of the catalyst (i.e. H-ZSM-5). The first calcination can be conducted at a temperature that is at least about 500° C., at least about 600° C., at least about 700° C., at least about 800° C., or at least about 900° C. A metal-promoted zeolite (e.g. Fe-ZSM-5) can be prepared from an ion-exchange of the catalyst in acid form (i.e. H-ZSM-5) and can be calcined at a temperature that is at least about 500° C., at least about 600° C., at least about 700° C., at least about 800° C., or at least about 900° C. The calcination temperature can be in the range of from about 500° C. to about 1000° C., from about 600° C. to about 1000° C., from about 700° C. to about 1000° C., from about 800° C. to about 1000° C., or from about 900° C. to about 1000° C., from about 500° C. to about 900° C., from about 500° C. to about 800° C., from about 500° C. to about 700° C., from about 520° C. to about 600° C., from about 530° C. to 580° C., or from about 540° C. to 560° C. The zeolite (e.g. Fe-ZSM-5) can then be activated using steam or argon gas at a temperature that is at least about 600° C., at least about 700° C., at least about 800° C., or at least about 900° C. The activation of the catalyst under an argon gas can be at a temperature in the range of from about 800° C. to about 1000° C., or from about 850° C. to about 950° C. The activation of the catalyst with steam under an argon gas can be at a temperature in the range of from about 600° C. to about 800° C., or from about 650° C. to about 700° C. Following activation, the catalyst is finally calcined under a nitrogen gas prior to use at a temperature that is at least about 600° C., at least about 700° C., at least about 800° C., or at least about 900° C. The calcination temperature can be in the range of from about 600° C. to about 1000° C., from about 600° C. to about 900° C., from about 700° C. to about 800° C., or from about 740° C. to about 760° C.

The hydroxylation processes can be conducted over a wide temperature range. Generally, gas comprising the 1,4-dichlorobenzene is contacted with the catalyst at a temperature in the range of from about 250° C. to about 550° C., from about 275° C. to about 500° C., from about 275° C. to about 400° C., from about 275° C. to about 375° C., from about 300° C. to about 500° C., from about 300° C. to about 450° C., from about 350° C. to about 400° C., from about 350° C. to about 450° C., from about 375° C. to about 425° C., or from about 385° C. to about 415° C.

Various oxidizing agents may be used in the hydroxylation processes. Suitable oxidizing agents include hydrogen peroxide, molecular oxygen, mixture of oxygen/hydrogen, mixture of oxygen/ammonia, and nitrous oxide. The mole ratio of oxidizing agent to 1,4-dichlorobenzene can be at least about 0.25:1, at least about 0.5:1, at least about 1:1, at least about 2:1, at least about 3:1, at least about 4:1, or at least about 5:1. The mole ratio of oxidizing agent to 1,4-dichlorobenzene can be in the range of from about 0.25:1 to about 10:1, from 0.5:1 to about 8:1, from 1:1 to about 5:1, from about 2:1 to about 10:1, from about 2:1 to about 5:1, from about 3:1 to about 10:1, or from about 3:1 to about 5:1.

The hydroxylation reaction can be conducted in the presence of an inert gas such as nitrogen or argon gas. In some cases, it has been found that reducing the oxygen concentration beneficially suppresses the formation of monochlorophenols. Accordingly, the hydroxylation reaction can be conducted in atmosphere that is essentially free of molecular oxygen.

The oxidation catalyst that is present in the reactor system can be situated in a variety of different ways. For example, the oxidation catalyst can be situated such that it is in contact with the feed and/or reaction product of the hydroxylation, generally so long as the oxidation catalyst does not cause any significant negative effects to the efficacy of the hydroxylation reaction (e.g., within the isomerization zone). Thus, one approach to this arrangement is mixing the oxidation catalyst with the hydroxylation catalyst (e.g., in a fixed bed comprising the catalysts in the hydroxylation zone). Another arrangement includes a stacked or staged reactor system configuration. In these embodiments, a first stage comprises the hydroxylation catalyst and a second stage comprises the oxidation catalyst, wherein the second stage is downstream of the first stage with respect to the direction of flow through the reactor system. Other approaches include incorporating or supporting the oxidation catalyst on the hydroxylation catalyst (i.e., as a co-catalyst). In these embodiments where the oxidation catalyst is in contact with the feed and/or hydroxylation reaction product, the temperature of the oxidation catalyst is typically maintained at a temperature of no less than about 220° C. (e.g., to prevent condensation of feed/product constituents on the catalysts).

The oxidation catalyst can be also positioned such that it is not in contact with the feed and/or reaction product of the hydroxylation. For example, in the staged reactor system configuration, the first stage and second stage can be configured such that the reaction product comprising 2,5-dichlorophenol can optionally bypass the second stage. A further approach involves transferring the hydroxylation catalyst from the hydroxylation zone to a catalyst regeneration zone wherein the catalyst regeneration zone comprises the oxidation catalyst.

The hydroxylation process for producing 2,5-dichlorophenol typically further comprises the step of regenerating the hydroxylation catalyst, wherein the hydroxylation catalyst comprises a chlorinated aromatic compound adsorbed thereon. The regeneration proceeds as discussed herein. For example, in various embodiments, regenerating the hydroxylation catalyst comprises heating the catalyst at an elevated temperature (e.g., of from about 400° C. to about 1000° C.) in the presence of oxygen to remove at least a portion of the chlorinated aromatic compound from the hydroxylation catalyst and produce a regenerated hydroxylation catalyst and a regeneration effluent; and contacting the regeneration effluent with the oxidation catalyst comprising the at least one metal oxide to form an oxidation effluent comprising carbon dioxide, water, and hydrochloric acid. The regeneration process can also further comprise a pre-cleaning step as described above to desorbing at least a portion of the chlorinated aromatic compound from the hydroxylation catalyst prior to the step of heating the hydroxylation catalyst at the elevated temperature. Any one of more of the pre-cleaning strategies discussed herein can be utilized. The chlorinated aromatic compounds desorbed during pre-cleaning can be collected and recycled back to the hydroxylation zone.

Prior to catalyst regeneration, the hydroxylation catalyst comprises one or more chlorinated aromatic compounds adsorbed thereon. In various embodiments, the chlorinated aromatic compound comprises at least one compound selected from the group consisting of 2,5-dichlorophenol; 2,4-dichlorophenol; 2-chlorophenol; 3-chlorophenol; and 4-chlorophenol; 1,4-dichlorobenzene; 1,2-dichlorobenzene; 1,3-dichlorobenzene; and oxidation and chlorination products thereof; and mixtures thereof.

Hydroxylation processes can further comprise separating at least a portion of the 2,5-dichlorophenol from other reaction product constituents. Processes for separating 2,5-dichlorophenol from mixtures include those described in U.S. Pat. Nos. 2,708,209 and 3,462,498, which are incorporated herein by reference. Additionally or alternatively, the hydroxylation processes of the present invention can further comprise the step of separating at least a portion of the 2,4-dichlorophenol from other reaction product constituents. One process for separating 2,4-dichlorophenol from a mixture is described in U.S. Pat. No. 5,118,876, which is incorporated herein by reference.

Separation of 2,5-dichlorophenol from the hydroxylation reaction product or conversely, separation 2,4-dichlorophenol from the hydroxylation reaction product produces a fraction that is enriched in 2,4-dichlorophenol. This fraction can be introduced to an isomerization process as described herein to further convert the 2,4-dichlorophenol to 2,5-dichlorophenol.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above processes without departing from the scope of the invention, it is intended that all matter contained in the above description shall be interpreted as illustrative and not in a limiting sense.

What is claimed is:

1. A process for regeneration of a heterogeneous process catalyst comprising a chlorinated aromatic compound adsorbed thereon, the process comprising:

desorbing at least a portion of the chlorinated aromatic compound from the heterogeneous process catalyst at a temperature no greater than about 350° C. prior to the step of heating the heterogeneous process catalyst at the temperature of from about 400° C. to about 1000° C. in the presence of oxygen to pre-clean the heterogeneous process catalyst;

heating the heterogeneous process catalyst having at least a portion of the chlorinated aromatic compound desorbed therefrom at a temperature of from about 400° C. to about 1000° C. in the presence of oxygen to remove at least a portion of the chlorinated aromatic compound from the heterogeneous process catalyst and produce a regenerated heterogeneous process catalyst and a regeneration effluent; and contacting the regeneration effluent with an oxidation catalyst comprising at least one metal oxide selected from the group consisting of vanadium oxide, chromium oxide, manganese oxide, and mixtures thereof to form an oxidation effluent comprising carbon dioxide, water, and hydrochloric acid, wherein the heterogeneous process catalyst comprises a zeolite.

2. The process of claim 1 wherein the at least one metal oxide comprises chromium oxide.

3. The process of claim 1 wherein the at least one metal oxide comprises vanadium oxide.

4. The process of claim 1 wherein the oxidation catalyst comprises the at least one metal oxide on a support.

5. The process of claim 4 wherein the support of the oxidation catalyst comprises at least one material selected from the group consisting of alumina, titania, silica, zirconia, carbon, zeolite, and combinations thereof.

6. The process of claim 4 wherein the support of the oxidation catalyst comprises titania.

7. The process of claim 1 wherein the oxidation catalyst is mixed with the heterogeneous process catalyst.

8. A process for regeneration of a heterogeneous process catalyst comprising a chlorinated aromatic compound adsorbed thereon, the process comprising:

heating the heterogeneous process catalyst at a temperature of from about 400° C. to about 1000° C. in the presence of oxygen to remove at least a portion of the chlorinated aromatic compound from the heterogeneous process catalyst and produce a regenerated heterogeneous process catalyst and a regeneration effluent; and contacting the regeneration effluent with an oxidation catalyst comprising at least one metal oxide selected from the group consisting of vanadium oxide, chromium oxide, manganese oxide, and mixtures thereof to form an oxidation effluent comprising carbon dioxide, water, and hydrochloric acid, wherein the oxidation catalyst is supported on the heterogeneous process catalyst and wherein the heterogeneous process catalyst comprises a zeolite.

9. The process of claim 1 wherein a first stage comprises the heterogeneous process catalyst and a second stage comprises the oxidation catalyst comprising the at least one metal oxide and wherein the second stage is downstream of the first stage.

10. The process of claim 1 wherein desorbing at least a portion of the chlorinated aromatic compound from the heterogeneous process catalyst comprises applying vacuum to the heterogeneous process catalyst.

11. The process of claim 1 wherein desorbing at least a portion of the chlorinated aromatic compound from the heterogeneous process catalyst comprises contacting the heterogeneous process catalyst with steam.

12. The process of claim 11 wherein the temperature of the steam is no greater than about 300° C.

13. The process of claim 8 wherein the at least one metal oxide comprises vanadium oxide.

14. The process of claim 1 wherein desorbing at least a portion of the chlorinated aromatic compound from the heterogeneous process catalyst is conducted in a non-oxidative atmosphere.

15. The process of claim 1 further comprising recycling at least a portion of the desorbed chlorinated aromatic compound to an isomerization reaction zone.

16. The process of claim 1 wherein the chlorinated aromatic compound comprises at least one compound selected from the group consisting of 2,3,4-trichlorophenol; 2,3,5-trichlorophenol; 2,3,6-trichlorophenol; 2,4,5-trichlorophenol; 2,4,6-trichlorophenol; 3,4,5-trichlorophenol; 2,3-dichlorophenol; 2,4-dichlorophenol; 2,5-dichlorophenol; 2,6-dichlorophenol; 3,4-dichlorophenol; 3,5-dichlorophenol; 2-chlorophenol; 3-chlorophenol; 4-chlorophenol; 1,2,3-trichlorobenzene; 1,2,4-trichlorobenzene; 1,3,5-trichlorobenzene; 1,2-dichlorobenzene; 1,3-dichlorobenzene; 1,4-dichlorobenzene; and oxidation and chlorination products thereof; and mixtures thereof.

17. A process for producing 2,5-dichlorophenol, the process comprising:

contacting a feed comprising 2,4-dichlorophenol with an isomerization catalyst comprising a zeolite in a reactor system comprising an isomerization zone to form a reaction product comprising 2,5-dichlorophenol, wherein the reactor system further comprises an oxidation catalyst comprising at least one metal oxide selected from the group consisting of vanadium oxide, chromium oxide, manganese oxide, and mixtures thereof; and regenerating the isomerization catalyst according to the process of claim 1, wherein the isomerization catalyst is the heterogeneous process catalyst comprising a chlorinated aromatic compound adsorbed thereon.

18. A process for producing 2,5-dichlorophenol, the process comprising:

contacting a feed comprising 2,4-dichlorophenol with an isomerization catalyst comprising a zeolite in a reactor system comprising an isomerization zone to form a reaction product comprising 2,5-dichlorophenol, wherein the reactor system further comprises an oxidation catalyst comprising at least one metal oxide selected from the group consisting of vanadium oxide, chromium oxide, manganese oxide, and mixtures thereof; and regenerating the isomerization catalyst according to the process of claim 8, wherein the isomerization catalyst is the heterogeneous process catalyst comprising a chlorinated aromatic compound adsorbed thereon.

19. A process for producing 2,5-dichlorophenol, the process comprising:

contacting a feed comprising 1,4-dichlorobenzene with an oxidizing agent in the presence of a hydroxylation catalyst comprising a zeolite in a reactor system comprising a hydroxylation zone to form a reaction product comprising 2,5-dichlorophenol, wherein the reactor system further comprises an oxidation catalyst comprising at least one metal oxide selected from the group consisting of vanadium oxide, chromium oxide, manganese oxide, and mixtures thereof; and regenerating the hydroxylation catalyst according to the process of claim 1, wherein the hydroxylation catalyst is the heterogeneous process catalyst comprising a chlorinated aromatic compound adsorbed thereon.

20. A process for producing 2,5-dichlorophenol, the process comprising:

contacting a feed comprising 1,4-dichlorobenzene with an oxidizing agent in the presence of a hydroxylation catalyst comprising a zeolite in a reactor system comprising a hydroxylation zone to form a reaction product comprising 2,5-dichlorophenol, wherein the reactor system further comprises an oxidation catalyst comprising at least one metal oxide selected from the group consisting of vanadium oxide, chromium oxide, manganese oxide, and mixtures thereof; and regenerating the hydroxylation catalyst according to the process of claim 8, wherein the hydroxylation catalyst is the heterogeneous process catalyst comprising a chlorinated aromatic compound adsorbed thereon.

\* \* \* \* \*